United States Patent
Hagiya

(10) Patent No.: US 7,459,588 B2
(45) Date of Patent: Dec. 2, 2008

(54) METHOD FOR PRODUCING UNSATURATED VICINAL DIOL COMPOUND

(75) Inventor: Koji Hagiya, Ibaraki (JP)

(73) Assignee: Sumitomo Chemical Company, Limited, tokyo (JP)

( * ) Notice: Subject to any disclaimer, the term of this patent is extended or adjusted under 35 U.S.C. 154(b) by 97 days.

(21) Appl. No.: 11/662,521

(22) PCT Filed: Sep. 9, 2005

(86) PCT No.: PCT/JP2005/017091

§ 371 (c)(1),
(2), (4) Date: Mar. 12, 2007

(87) PCT Pub. No.: WO2006/030877

PCT Pub. Date: Mar. 23, 2006

(65) Prior Publication Data

US 2008/0114185 A1 May 15, 2008

(30) Foreign Application Priority Data

Sep. 14, 2004 (JP) ............................. 2004-266446

(51) Int. Cl.
*C07C 27/00* (2006.01)
(52) U.S. Cl. .................................................. 568/858
(58) Field of Classification Search ................ 568/858
See application file for complete search history.

(56) References Cited

U.S. PATENT DOCUMENTS

| 5,250,743 A | 10/1993 | Boaz |
| 2005/0090688 A1 | 4/2005 | Hagiya |

FOREIGN PATENT DOCUMENTS

| DE | 44 29 699 A1 | 3/1995 |
| JP | 2000-159693 | 6/2000 |
| WO | WO 91/15469 | 10/1991 |

*Primary Examiner*—Jafar Parsa
(74) *Attorney, Agent, or Firm*—Foley & Lardner LLP

(57) ABSTRACT

A method for producing an unsaturated vicinal diol compound represented by the formula (2):

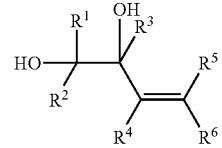

(2)

wherein $R^1$, $R^2$, $R^3$, $R^4$, $R^5$ and R are the same or different and each independently represent a hydrogen atom; a C1-C20 alkyl group which may be substituted with a halogen atom or atoms, a C1-C6 alkoxy group or groups, a C2-C7 alkoxycabonyl group or groups, a C6-C10 aryl group or groups, or a carboxyl group or groups; or a C6-C10 aryl group which may be substituted with a halogen atom or atoms, a C1-C6 alkoxy group or groups, a C6-C10 aryl group or groups, or a carboxyl group or groups; which comprises reacting an unsaturated epoxy compound represented by the formula (1):

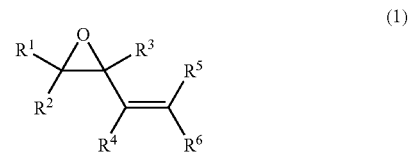

(1)

wherein $R^1$, $R^2$, $R^3$, $R^4$, $R^5$ and $R^6$ are the same as defined above, with water in the presence of a silicate containing at least one element selected from a group 5 element and a group 6 element of the long periodic table as a constituent.

8 Claims, No Drawings

METHOD FOR PRODUCING UNSATURATED VICINAL DIOL COMPOUND

TECHNICAL FIELD

The present invention relates to a method for producing an unsaturated vicinal diol compound.

BACKGROUND ART

Unsaturated vicinal diol compounds are important compounds as raw materials of bioactive substance such as pharmaceuticals and agrichemicals, and monomers for production of functional polymers as described in U.S. Pat. No. 5,336,815. As methods for producing the unsaturated vicinal diol compound, a method comprising a reaction of an unsaturated epoxy compound with water in the presence of a sulfuric acid catalyst is described in U.S. Pat. No. 5,250,743. A method comprising a reaction of an unsaturated epoxy compound with water in the presence of an acidic resin is described in WO 91/15469. A method comprising a reaction of an unsaturated epoxy compound with water in the presence of rhenium oxide catalyst is described in DE 4429700. A method comprising a reaction of an unsaturated epoxy compound with water in the presence of titanium silicate or zirconium silicate is described in DE 4429699.

DISCLOSURE OF THE INVENTION

The present invention provides a method for producing an unsaturated vicinal diol compound represented by the formula (2):

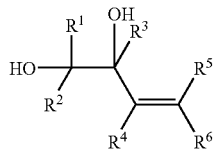

(2)

wherein $R^1$, $R^2$, $R^3$, $R^4$, $R^5$ and $R^6$ are the same or different and each independently represent a hydrogen atom; a C1-C20 alkyl group which may be substituted with a halogen atom or atoms, a C1-C6 alkoxy group or groups, a C2-C7 alkoxycarbonyl group or groups, a C6-C10 aryl group or groups, or a carboxyl group or groups; or a C6-C10 aryl group which may be substituted with a halogen atom or atoms, a C1-C6 alkoxy group or groups, a C6-C10 aryl group or groups, or a carboxyl group or groups, which comprises reacting an unsaturated epoxy compound represented by the formula (1):

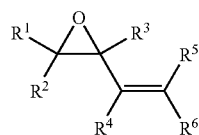

(1)

wherein $R^1$, $R^2$, $R^3$, $R^4$, $R^5$ and $R^6$ are the same as defined above, with water in the presence of a silicate containing at least one element selected from a group 5 element and a group 6 element of the long periodic table as a constituent.

BEST MODE FOR CARRYING OUT THE PRESENT INVENTION

In the present invention, the silicate containing at least one element selected from a group 5 element and a group 6 element of the long periodic table as a constituent (hereinafter, simply referred to as the metal-containing silicate) is not particularly limited as far as it is a silicate containing the group 5 element of the long periodic table, the group 6 element of the long periodic table or the both elements thereof as a constituent.

Examples of the group 5 element of the long periodic table include vanadium, niobium, tantalum and the like. Examples of the group 6 element of the long periodic table include tungsten, molybdenum, chromium and the like. Preferred are vanadium, molybdenum and tungsten, and more preferred are vanadium and molybdenum.

The metal-containing silicate can be produced by a method comprising reacting a metal oxide containing at least one element selected from the group 5 element and the group 6 element of the long periodic table as a constituent with a silicon compound in the presence of an organic template, followed by washing or calcining the obtained solid as described in EP 1473275 A, Applied Catalysis A: General 179, 11 (1999), and J. Chem. Soc., Chem. Commun., 2231 (1995). Among them, a metal-containing silicate produced by using a metal oxide which is obtained by reacting at least one compound selected from a group 5 metal of the long periodic table, a group 6 metal of the long periodic table, a compound containing the group 5 element of the long periodic table and a compound containing the group 6 element of the long periodic table with hydrogen peroxide is preferable as the metal oxide containing at least one element selected from the group 5 element and the group 6 element of the long periodic table as a constituent. The method for producing the metal-containing silicate produced by using the metal oxide which is obtained by reacting at least one compound selected from a group 5 metal of the long periodic table, a group 6 metal of the long periodic table, a compound containing the group 5 element of the long periodic table and a compound containing the group 6 element of the long periodic table (hereinafter, simply referred to as the metal or compound) with hydrogen peroxide will be illustrated below.

Examples of the group 5 metal of the long periodic table include vanadium metal, niobium metal and tantalum metal. Examples of the group 6 metal of the long periodic table include tungsten metal, molybdenum metal and chromium metal. Examples of the compound containing the group 5 element of the long periodic table as a constituent include a vanadium compound such as vanadium oxide, ammonium vanadate, vanadium carbonyl complex, vanadium sulfate and vanadium sulfate ethylene diamine complex; a niobium compound such as niobium oxide, niobium chloride and niobium carbonyl complex; and a tantalum compound such as tantalum oxide and tantalum chloride. Examples of the compound containing the group 6 element of the long periodic table as a constituent include a tungsten compound such as tungsten boride, tungsten carbide, tungsten oxide, ammonium tungstate and tungsten carbonyl complex; a molybdenum compound such as molybdenum boride, molybdenum oxide, molybdenum chloride, molybdenum carbonyl complex; and a chromium compound such as chromium oxide and chromium chloride.

Among the metals or compounds, tungsten metal, the tungsten compound, molybdenum metal, the molybdenum compound, vanadium metal and the vanadium compound are preferable, and molybdenum metal, the molybdenum compound, vanadium metal and the vanadium compound are more preferable.

The metals or compounds may be used alone, or two or more thereof may be used. Among the metals or compounds, there are metals or compounds having hydrates and the hydrates may be used or anhydrous one may be used for the present invention.

The metal oxide is obtained by reacting the metal or compound with hydrogen peroxide. As hydrogen peroxide, an aqueous solution is usually used. A solution of hydrogen peroxide in an organic solvent may be used and it is preferred to use the aqueous hydrogen peroxide solution from the viewpoint of easier handling. The concentration of hydrogen peroxide in the aqueous hydrogen peroxide solution or in the solution of hydrogen peroxide in the organic solvent is not particularly limited, but in view of volume efficacy and safety, the practical concentration is 1 to 60% by weight. As the aqueous hydrogen peroxide solution, a commercially available aqueous hydrogen peroxide solution is usually used as it is, or if necessary, it may be used after adjusting the concentration by dilution or concentration. The solution of hydrogen peroxide in the organic solvent can be prepared by extracting the aqueous hydrogen peroxide solution with the organic solvent, or distilling the solution in the presence of the organic solvent.

The amount of hydrogen peroxide to be used is usually 3 moles or more, preferably 5 moles or more relative to 1 mole of the metal or compound, and the upper limit of the amount is not particularly defined.

The reaction of the metal or compound with hydrogen peroxide is usually carried out in an aqueous solution. The reaction may be carried out in an organic solvent, for example, an ether solvent such as diethyl ether, methyl tert-butyl ether and tetrahydrofuran, an ester solvent such as ethyl acetate, an alcohol solvent such as methanol, ethanol and tert-butanol, a nitrile solvent such as acetonitrile and propionitrile, or in a mixture of the organic solvent and water.

The reaction of the metal or compound with hydrogen peroxide is usually carried out by contacting both of them, and in order to improve efficacy of contact between the metal or compound, and hydrogen peroxide, preferably, the reaction is carried out with stirring so as to sufficiently disperse the metal or compound in a solution for preparing the metal oxide. The reaction temperature is usually −10 to 100° C.

By reacting the metal or compound with hydrogen peroxide in water, in the organic solvent, or in the mixed solvent of water and the organic solvent, all or a part of the metal or compound is dissolved, whereby, a homogeneous solution or slurry containing the metal oxide can be prepared. The metal oxide may be isolated from the homogeneous solution or slurry, for example, by concentration or filtration followed to preparing a metal-containing silicate, and the homogeneous solution or slurry may be used as it is for preparing the metal-containing silicate.

As the silicon compound, a tetraalkoxysilane such as tetramethoxysilane, tetraethoxysilane and tetraisopropoxysilane is usually used. The silicon compound is usually used in such an amount that silicon atoms are 4 moles or more relative to 1 mole of the metal atom of the above-mentioned metal oxide, and the upper limit thereof is not particularly defined.

Examples of the organic template include an alkylamine, a quaternary ammonium salt and a nonionic surfactant, and the alkylamine and the quaternary ammonium salt are preferable.

Examples of the alkylamine include a primary amine wherein a hydrogen atom of ammonia is substituted with an alkyl group having 8 to 20 carbon atoms such as octylamine, nonylamine, decylamine, undecylamine, dodecylamine, tridecylamine, tetradecylamine and eicosylamine; a secondary amine wherein one of hydrogen atoms of the amino group of the above-mentioned primary amine is substituted with a lower alkyl group having 1 to 6 carbon atoms such as a methyl group; and a tertiary amine wherein a hydrogen atoms of the amino group of the above-mentioned secondary amine is substituted with a lower alkyl group having 1 to 6 carbon atoms, and the primary amine is preferable.

As the quaternary ammonium salt, those consisting of a quaternary ammonium ion wherein four hydrogen atoms of the ammonium ion ($NH_4^+$) are substituted with same or different four alkyl groups having 1 to 18 carbon atoms and an anion such as a hydroxide ion, a chloride ion and a bromide ion are exemplified. Specific examples thereof include a quaternary ammonium hydroxide salt such as tetraethylammonium hydroxide, tetrapropylammonium hydroxide, tetrabutylammonium hydroxide and trimethyloctylammonium hydroxide; a quaternary ammonium chloride salt such as tetraethylammonium chloride, tetrapropylammonium chloride, tetrabutylammonium chloride and trimethyloctylammonium chloride; and a quaternary ammonium bromide salt such as tetraethylammonium bromide, tetrapropylammonium bromide, tetrabutylammonium bromide and trimethyloctylammonium bromide, and the quaternary ammonium hydroxide is preferable.

Examples of the nonionic surfactant include polyethylene glycol.

The organic template may be used as it is and by mixing with water or a hydrophilic solvent described below. The amount of the organic template to be used is usually 0.03 to 1 mole relative to 1 mole of the silicon compound.

The reaction of the above-mentioned metal oxide with the silicon compound in the presence of the organic template is usually conducted by mixing three components in the presence of a solvent. Examples of the solvent include water or the hydrophilic solvent alone or a mixture thereof and, water and mixtures of water and the hydrophilic solvent are preferable. Examples of the hydrophilic solvent include a hydrophilic alcohol solvent such as methanol, ethanol and isopropanol; a hydrophilic nitrile solvent such as acetnitrile; and a hydrophilic ether solvent such as dioxane, and the hydrophilic alcohol solvent is preferable, and methanol or ethanol is more preferable. The amount of the solvent to be used is usually 1 to 1000 parts by weight relative to 1 part by weight of the organic template.

The reaction temperature is usually 0 to 200° C.

After completion of the reaction, for example, the reaction product is separated by filtration from the reaction liquid, and the metal-containing silicate can be produced by washing or calcining the separated reaction product. In case of washing the separated reaction product, examples of the washing solvent include an alcohol solvent such as methanol and ethanol, and water. The amount thereof to be used is not particularly limited. In the case of calcining the separated reaction product, the calcination temperature is usually 300 to 700° C., preferably 500 to 600° C., and the calcinations time is usually 0.5 to 20 hours. The separated reaction product may be calcinated after washing.

The metal-containing silicate thus obtained usually has pores of which the average micropore diameter is 4 to 100 Å (calculated by BHJ method based on the result measured by the nitrogen adsorption method) and the specific surface area thereof is usually 100 $m^2/g$ or more (calculated by BET multipoint method ($p/p_0$=0.1) based on the result measured by the nitrogen adsorption method).

Next, the method for producing the unsaturated vicinal diol compound represented by the formula (2) (hereinafter, simply referred to as the unsaturated vicinal diol compound (2)) by reacting the unsaturated epoxy compound represented by the formula (1) (hereinafter, simply referred to as the unsaturated epoxy compound (1)) with water in the presence of the metal-containing silicate.

In the formula of the unsaturated epoxy compound (1), $R^1$, $R^2$, $R^3$, $R^4$, $R^5$ and $R^6$ are the same or different and each independently represent a hydrogen atom; a C1-C20 alkyl group which may be substituted with a halogen atom or atoms, a C1-C6 alkoxy group or groups, a C2-C7 alkoxycabonyl group or groups, a C6-C10 aryl group or groups, or a carboxyl group or groups; or a C6-C10 aryl group which may be substituted with a halogen atom or atoms, a C1-C6 alkoxy group or groups, a C6-C10 aryl group or groups, or a carboxyl group or groups.

Examples of the halogen atom include a fluorine, chlorine and bromine atom. Examples of the C1-C6 alkoxy group include a methoxy, ethoxy, n-propoxy, isopropoxy, n-butoxy, tert-butoxy and n-hexyloxy group.

In the present invention, carbon number of the alkoxycarbonyl group means carbon number of whole alkoxycarbonyl group containing carbonyl carbon. Examples of the C2-C7 alkoxycabonyl group include a methoxycarbonyl, ethoxycarbonyl and isopropoxycarbonyl group.

Examples of the C6-C10 aryl group include a phenyl, 2-methylphenyl, 4-methylphenyl and naphthyl group.

Examples of the C1-C20 alkyl group which may be substituted with a halogen atom or atoms, a C1-C6 alkoxy group or groups, a C2-C7 alkoxycabonyl group or groups, a C6-C10 aryl group or groups, or a carboxyl group or groups include a methyl, ethyl, n-propyl, isopropyl, n-butyl, isobutyl, sec-butyl, tert-butyl, n-pentyl, n-decyl, cyclopropyl, 2,2-dimethylcyclopropyl, cyclopentyl, cyclohexyl, menthyl, chloromethyl, fluoromethyl, trifluoromethyl, methoxymethyl, ethoxymethyl, methoxyethyl, methoxycarbonylmethyl and benzyl group.

Examples of the C6-C10 aryl group which may be substituted with a halogen atom or atoms, a C1-C6 alkoxy group or groups, a C6-C10 aryl group or groups, or a carboxyl group or groups include a phenyl, naphthyl, 2-methylphenyl, 4-chlorophenyl, 4-methylphenyl, 4-methoxyphenyl, 4-phenoxyphenyl and 4-carboxyphenyl group.

Examples of the unsaturated epoxy compound (1) include 1,2-epoxy-3-butene, 1,2-epoxy-2-methyl-3-butene, 1,2-epoxy-1-phenyl-3-butene, 2,3-epoxy-2-methyl-4-pentene, 2,3-epoxy-1-phenyl-4-pentene, 2,3-epoxy-4-pentene, 2,3-epoxy-2,5-dimethyl-4-hexene and 2,3-epoxy-4-hexene.

Among the unsaturated epoxy compound (1), there are those having an asymmetric carbon atom within the molecule and having an optical isomer. Each of the optical isomer alone and a mixture thereof can be used in the present invention.

The unsaturated epoxy compound (1) can be produced according to a known method such as a method for oxidizing a diene compound with oxygen in the presence of a silver-containing catalyst (e.g. U.S. Pat. Nos. 4,897,498 and 4,950,773).

The amount of the metal-containing silicate to be used is usually 0.001 part by weight or more per 1 part by weight of the unsaturated epoxy compound (1). There is no specific upper limit and it is practically 5 parts by weight or less per 1 part by weight of the unsaturated epoxy compound (1) considering economical viewpoint.

The amount of water to be used is usually 1 mole or more relative to 1 mole of the unsaturated epoxy compound (1). There is no specific upper limit and large excess amount thereof, for example, 500 moles relative to 1 mole of the unsaturated compound, can be used also to serve as the solvent.

The reaction of the unsaturated epoxy compound (1) and water is usually carried out in the absence of a solvent or in water solvent, and the reaction may be carried out in the presence of an organic solvent. Examples of the organic solvent include an ether solvent such as diethyl ether, methyl tert-butyl ether and tetrahydrofuran; an ester solvent such as ethyl acetate; a tertiary alcohol solvent such as tert-butanol; and a nitrile solvent such as acetonitrile and propionitrile. The amount of the organic solvent to be used is not particularly limited, and it is practically 100 parts by weight or less per 1 part by weight of the unsaturated epoxy compound (1) considering volume efficacy.

The reaction of the unsaturated epoxy compound (1) and water is usually conducted by mixing the unsaturated epoxy compound (1), water and the metal-containing silicate, and the mixing order is not particularly limited.

The reaction is usually conducted under ordinary pressure conditions and may be conducted under reduced pressure conditions or pressurized conditions. The reaction temperature is usually 0 to 100° C.

The progress of the reaction can be confirmed by a conventional analytical means such as gas chromatography, high performance liquid chromatography, thin layer chromatography, nuclear magnetic resonance spectrum analysis and infrared adsorption spectrum analysis.

After completion of the reaction, the unsaturated vicinal diol compound (2) can be isolated by filtering the reaction liquid to separate the metal-containing silicate and then concentrating or crystallizing the filtrate obtained. The unsaturated vicinal diol compound (2) can be also isolated by, if necessary, adding water and/or a water-insoluble organic solvent to the above-mentioned filtrate, followed by extracting and concentrating the organic layer obtained. Examples of the water-insoluble organic solvent include a halogenated hydrocarbon solvent such as dichloromethane, chloroform and chlorobenzene; an ether solvent such as diethyl ether and methyl tert-butyl ether: and an ester solvent such as ethyl acetate, and the amount thereof to be used is not particularly limited.

The unsaturated vicinal diol compound (2) obtained may be further purified by conventional purification means such as distillation and column chromatography.

Examples of the unsaturated vicinal diol compound (2) thus obtained include 3-butene-1,2-diol, 2-methyl-3-butene-1,2-diol, 1-phenyl-3-butene-1,2-diol, 2-methyl-4-pentene-2,3-diol, 1-phenyl-4-pentene-2,3-diol, 4-pentene-2,3-diol, 2,5-dimethyl-4-hexene-2,3-diol and 4-hexene-2,3-diol.

When an optically active unsaturated epoxy compound (1) is used, an optically active unsaturated vicinal diol compound (2) is usually obtained.

The metal-containing silicate separated from the reaction liquid can be used again in the reaction of the unsaturated epoxy compound (1) and water.

EXAMPLES

The present invention will be further illustrated by Examples in detail below, but the present invention is not limited by these Examples. The yield was calculated from the result of gas chromatography internal standard method.

Each of the specific surface area and the average micropore diameter of the metal-containing silicate obtained were measured at 150° C. under a degassed condition of $1.35 \times 10^{-5}$ Kg/cm$^{-2}$ (equivalent of 0.013 kPa) by the nitrogen adsorption method using Autosorb-6 manufactured by Quantachrome Instruments, and the specific surface area and the average micropore diameter thereof were calculated using BET multipoint method ($p/p_0$=0.1) and BHJ method respectively.

Reference Example 1

To a 500 mL flask equipped with a stirrer, 5 g of a tungsten metal powder and 25 g of ion-exchanged water were added, and an inner temperature was adjusted to 40° C. 15 g of a 60% by weight aqueous hydrogen peroxide solution was added dropwise thereto over 30 minutes, and then the mixture was maintained at the same temperature for 1 hour to obtain a solution containing tungsten oxide. To the solution containing tungsten oxide, 75 g of ion-exchanged water and 80 g of ethanol were added, and then 41.6 g of tetraethoxysilane was added dropwise thereto over 10 minutes. Further, 20 g of 40% by weight aqueous tetrabutylammonium hydroxide solution was added dropwise thereto at the same temperature over 10 minutes. Then, the mixture was cooled to an inner temperature of 25° C. and stirring was continued at the same temperature, and solid was precipitated in about 30 minutes to form slurry. After stirring and maintaining at the same temperature for 24 hours, solid was collected by filtration. Solid filtrated was washed twice with 100 g of ion-exchanged water, and then dried at 130° C. for 24 hours to obtain 38.0 g of the white solid. The white solid obtained was calcined at 550° C. for 6 hours to obtain 16.5 g of the white tungsten-containing silicate.

XRD spectrum: A broad peak having an apex at a d value of 3.77 Å is observed. A peak assignable to tungsten oxide is not observed.

IR spectrum (KBr)
$v_{max}$: 3478, 1638, 1078, 960, 806, 557 cm$^{-1}$
Elemental analysis value; W: 9.8%, Si: 39.5%
Specific surface area: 543 m$^2$/g, Average micropore diameter: 16 Å

Reference Example 2

To a 500 mL flask equipped with a stirrer, 5 g of a tungsten metal powder and 25 g of ion-exchanged water were added, and an inner temperature was adjusted to 40° C. 15 g of a 60% by weight aqueous hydrogen peroxide solution was added dropwise thereto over 30 minutes, and then the mixture was maintained at the same temperature for 2 hours to obtain a solution containing tungsten oxide. To the solution containing tungsten oxide, 75 g of ion-exchanged water and 80 g of ethanol were added, and then 41.6 g of tetraethoxysilane was added thereto at an inner temperature of 40° C. over 10 minutes. Further, 40 g of a 10% by weight tetrapropylammonium hydroxide solution was added dropwise thereto at the same temperature over 10 minutes. Then, the mixture was cooled to an inner temperature of 25° C. and stirring was continued at the same temperature. Solid was precipitated in about 30 minutes to form slurry. After stirring and maintaining at the same temperature for 24 hours, solid was collected by filtration. Solid filtrated was washed twice with 100 g of ion-exchanged water and dried at 130° C. for 24 hours to obtain 38.0 g of white solid. The white solid obtained was calcined at 550° C. for 6 hours to obtain 17.3 g of a white tungsten-containing silicate.

XRD spectrum: A broad peak having an apex at a d value of 3.76 Å is observed. A sharp peak assignable to tungsten oxide is slightly observed.

IR spectrum (KBr)
$v_{max}$: 3480, 1638, 1078, 956, 800 cm$^{-1}$
Elemental analysis value; W: 11.0%, Si: 31.4%
Specific surface area: 573 m$^2$/g, Average micropore diameter: 22 Å

Reference Example 3

To a 500 mL flask equipped with a stirrer, 2 g of a molybdenum metal powder and 25 g of ion-exchanged water were added, and an inner temperature was adjusted to 40° C. 15 g of a 60% by weight aqueous hydrogen peroxide solution was added dropwise thereto over 1 hour, and then the mixture was maintained at the same temperature for 1 hour to obtain a solution containing molybdenum oxide. To the solution containing molybdenum oxide, 75 g of ion-exchanged water and 80 g of ethanol were added, and then 41.6 g of tetraethoxysilane was added thereto at an inner temperature of 40° C. over 10 minutes. Further, 10 g of dodecylamine was added dropwise thereto at the same temperature over 10 minutes. Solid was immediately precipitated to form slurry. The mixture was cooled to an inner temperature of 25° C. and stirred and maintained for 24 hours, and then solid was collected by filtration. Solid filtrated was washed twice with 100 g of ion-exchanged water, dried at 110° C. for 6 hours and calcined at 550° C. for 6 hours to obtain 15.5 g of a white molybdenum-containing silicate.

XRD spectrum: A mixed spectrum of a broad peak having an apex at a d value of 3.8 Å and a sharp peak assignable to molybdenum oxide is observed.

IR spectrum (KBr)
$v_{max}$: 3470, 1640, 1090, 956, 915, 802 cm$^{-1}$
Elemental analysis value; Mo: 13.9%, Si: 32.4%
Specific surface area: 171 m$^2$/g, Average micropore diameter: 73 Å

It was confirmed that the white molybdenum-containing silicate obtained had molybdenum oxide from these results.

Reference Example 4

To a 500 mL flask equipped with a stirrer, 2.5 g of a molybdenum metal powder and 25 g of ion-exchanged water were added, and an inner temperature was adjusted to 40° C. 15 g of a 60% by weight aqueous hydrogen peroxide solution was added dropwise thereto over 1 hour, and then the mixture was maintained at the same temperature for 1 hour to obtain a solution containing molybdenum oxide. To the solution containing molybdenum oxide, 75 g of ion-exchanged water and 80 g of ethanol were added, and then 41.6 g of tetraethoxysilane was added thereto at an inner temperature of 40° C. over 10 minutes. Further, 20 g of a 40% by weight tetrabutylammonium hydroxide solution was added dropwise thereto over 10 minutes. Then, stirring was continued at the same temperature and solid was precipitated in about 15 minutes to form slurry. 200 g of ion-exchanged water was added to slurry. The mixture was cooled to an inner temperature of 25° C. and stirred and maintained at the same temperature for 24 hours. Then, solid was collected by filtration. Solid filtrated was washed twice with 100 g of ion-exchanged water, dried at 110° C. for 6 hours and calcined at 550° C. for 6 hours to obtain 15.9 g of a white molybdenum-containing silicate.

XRD spectrum: A broad peak having an apex at a d value of 3.79 Å is observed. A sharp peak assignable to tungsten oxide is not observed.

IR spectrum (KBr)
$v_{max}$: 3470, 1640, 1080, 956, 913, 796 cm$^{-1}$
Elemental analysis value; Mo: 5.22%, Si: 37.0%

Specific surface area: 649 m²/g, Average micropore diameter: 22 Å

Reference Example 5

To a 500 mL flask equipped with a stirrer, 1.3 g of a vanadium metal powder and 25 g of ion-exchanged water were added, and an inner temperature was adjusted to 40° C. 15 g of a 30% by weight aqueous hydrogen peroxide solution was added dropwise thereto over 30 minutes, and then the mixture was maintained at the same temperature for 1 hour to obtain a solution containing vanadium oxide. To the solution containing vanadium oxide, 75 g of ion-exchanged water and 80 g of ethanol were added, and then 41.6 g of tetraethoxysilane was added thereto at an inner temperature of 40° C. over 10 minutes. Further, 40 g of a 40% by weight tetra-n-propylamine solution was added dropwise thereto over 10 minutes. Then, the mixture was cooled to an inner temperature of 25° C. and stirring was continued and solid was precipitated in about 30 minutes to form slurry. The slurry was stirred and maintained at the same temperature for 24 hours. Then, solid was collected by filtration. Solid filtrated was washed twice with 100 g of ion-exchanged water, dried at 130° C. for 8 hours and calcined at 550° C. for 6 hours to obtain 16.0 g of a brown vanadium-containing silicate.

XRD spectrum: A broad peak having an apex at a d value of 3.85 Å is observed. A sharp peak assignable to vanadium oxide is not observed.

IR spectrum (KBr)
$\nu_{max}$: 1050, 956, 794, 629 cm$^{-1}$
Elemental analysis value; V: 5.56%, Si: 36.1%
Specific surface area: 708 m²/g, Average micropore diameter: 27 Å

Example 1

To a 50 mL flask equipped with a magnetic stirrer and a reflux condenser, 30 mg of the molybdenum-containing silicate obtained in the above-mentioned Reference Example 4, 310 mg of 1,2-epoxy-3-butene and 3 g of distilled water were added. The resultant mixture was stirred at an inner temperature of 25° C. for 5 hours to effect reaction. 10 g of tetrahydrofuran was added to the reaction liquid obtained to obtain a solution containing 3-butene-1,2-diol. The yield of 3-butene-1,2-diol was 93% and the yield of 2-butene-1,4-diol was 5%.

Example 2

According to a similar manner as that of Example 1, the reaction was conducted except that the vanadium-containing silicate obtained in the above-mentioned Reference Example 5 was used in place of the molybdenum-containing silicate obtained in the above-mentioned Reference Example 4 and 300 mg of 1,2-epoxy-3-butene was used. The yield of 3-butene-1,2-diol was 94% and the yield of 2-butene-1,4-diol was 6%.

Example 3

According to a similar manner as that of Example 1, the reaction was conducted except that the molybdenum-containing silicate obtained in the above-mentioned Reference Example 3 was used in place of the molybdenum-containing silicate obtained in the above-mentioned Reference Example 4 and 330 mg of 1,2-epoxy-3-butene was used. The yield of 3-butene-1,2-diol was 95% and the yield of 2-butene-1,4-diol was 4%.

Example 4

According to a similar manner as that of Example 1, the reaction was conducted except that the tungsten-containing silicate obtained in the above-mentioned Reference Example 1 was used in place of the molybdenum-containing silicate obtained in the above-mentioned Reference Example 4. The yield of 3-butene-1,2-diol was 81% and the yield of 2-butene-1,4-diol was 5%.

Example 5

According to a similar manner as that of Example 1, the reaction was conducted except that the tungsten-containing silicate obtained in the above-mentioned Reference Example 2 was used in place of the molybdenum-containing silicate obtained in the above-mentioned Reference Example 4. The yield of 3-butene-1,2-diol was 82% and the yield of 2-butene-1,4-diol was 2%. 3-buten-1,2-epoxyde was remained in 9%.

Example 6

Into a 50 mL flask equipped with a magnetic stirrer and a reflux condenser, 30 mg of the vanadium-containing silicate obtained in the above-mentioned Reference Example 5, 300 mg of 1,2-epoxy-3-butene and 3 g of distilled water were charged. The resultant mixture was stirred at an inner temperature of 25° C. for 5 hours to effect reaction. 10 g of tetrahydrofuran was added to the reaction liquid obtained, and then the vanadium-containing silicate was separated by decantation to obtain a solution containing 3-butene-1,2-diol. The yield of 3-butene-1,2-diol was 94% and the yield of 2-butene-1,4-diol was 5%.

Example 7

Into a 50 mL flask equipped with a magnetic stirrer and a reflux condenser, all amount of the vanadium-containing silicate separated by decantation in the above-mentioned Example 6, 300 mg of 1,2-epoxy-3-butene and 3 g of distilled water were charged. The resultant mixture was stirred at an inner temperature of 25° C. for 5 hours to effect reaction. 10 g of tetrahydrofuran was added to the reaction liquid obtained to obtain a solution containing 3-butene-1,2-diol. The yield of 3-butene-1,2-diol was 87% and the yield of 2-butene-1,4-diol was 8%. 1,2-epoxy-3-butene was remained in 5%.

The invention claimed is:

1. A method for producing an unsaturated vicinal diol compound represented by the formula (2):

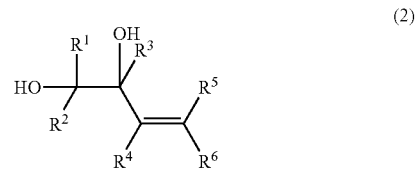

(2)

wherein R¹, R², R³, R⁴, R⁵ and R⁶ are the same or different and each independently represent a hydrogen atom;
a C1-C20 alkyl group which may be substituted with a halogen atom or atoms, a C1-C6 alkoxy group or groups, a C2-C7 alkoxycabonyl group or groups, a C6-C10 aryl group or groups, or a carboxyl group or groups; or a C6-C10 aryl group which may be substituted with a halogen atom or atoms, a C1-C6 alkoxy group or groups, a C6-C10 aryl group or groups, or a carboxyl group or groups, which comprises reacting an unsaturated epoxy compound represented by the formula (1):

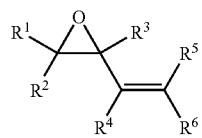

wherein $R^1$, $R^2$, $R^3$, $R^4$, $R^5$ and $R^6$ are the same as defined above, with water in the presence of a silicate containing at least one element selected from a group 5 element and a group 6 element of the long periodic table as a constituent.

2. The method according to claim 1, wherein the silicate is a silicate containing at least one element selected from vanadium, molybdenum and tungsten as a constituent.

3. The method according to claim 1, wherein the unsaturated epoxy compound represented by the formula (1) is 1,2-epoxy-3-butene and the unsaturated vicinal diol compound represented by the formula (2) is 3-butene-1,2-diol.

4. The method according to claim 1, wherein the silicate containing at least one element selected from a group 5 element and a group 6 element of the long periodic table as a constituent is a metal-containing silicate obtained by reacting a metal oxide, which is obtained by reacting at least one compound selected from a group 5 metal of the long periodic table, a group 6 metal of the long periodic table, a compound containing a group 5 element of the long periodic table and a compound containing a group 6 element of the long periodic table, with hydrogen peroxide, with a silicon compound in the presence of an organic template.

5. The method according to claim 4, wherein the metal-containing silicate is a metal-containing silicate obtained by separating the reaction product from the reaction liquid after the completion of the reaction, and washing or calcining the separated reaction product.

6. The method according to claim 4, wherein the group 5 metal of the long periodic table, the group 6 metal of the long periodic table, the compound containing a group 5 element of the long periodic table and the compound containing a group 6 element of the long periodic table is tungsten metal, molybdenum metal, vanadium metal, a tungsten compound, a molybdenum compound or a vanadium compound.

7. The method according to claim 4, wherein the organic template is an alkylamine, a quaternary ammonium salt or a nonionic surfactant.

8. The method according to claim 4, wherein the organic template is an alkylamine or a quaternary ammonium salt.

* * * * *